(12) United States Patent
Kakimoto et al.

(10) Patent No.: US 10,646,211 B2
(45) Date of Patent: May 12, 2020

(54) TREATMENT METHOD AND MEDICAL DEVICE

(71) Applicant: TERUMO KABUSHIKI KAISHA, Tokyo (JP)

(72) Inventors: Takuya Kakimoto, Fujinomiya (JP); Shinya Sawada, Fujinomiya (JP); Koji Yabe, Fuji (JP); Masumi Takano, Fujinomiya (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 189 days.

(21) Appl. No.: 15/423,727

(22) Filed: Feb. 3, 2017

(65) Prior Publication Data
US 2017/0224464 A1 Aug. 10, 2017

(30) Foreign Application Priority Data
Feb. 8, 2016 (JP) ................................. 2016-022256

(51) Int. Cl.
| | | |
|---|---|---|
| *A61B 17/00* | (2006.01) | |
| *A61B 17/34* | (2006.01) | |
| *A61B 50/30* | (2016.01) | |
| *A61B 90/00* | (2016.01) | |
| *A61F 2/24* | (2006.01) | |

(52) U.S. Cl.
CPC ...... *A61B 17/0057* (2013.01); *A61B 17/3468* (2013.01); *A61B 50/30* (2016.02); *A61B 2017/00243* (2013.01); *A61B 2017/00349* (2013.01); *A61B 2017/00561* (2013.01); *A61B 2017/00575* (2013.01); *A61B 2017/00597* (2013.01); *A61B 2017/00623* (2013.01); *A61B 2090/0815* (2016.02); *A61F 2/2481* (2013.01); *A61F 2002/2484* (2013.01)

(58) Field of Classification Search
CPC ................................ C12N 11/00; A61B 17/00
See application file for complete search history.

(56) References Cited

U.S. PATENT DOCUMENTS

| | | | | |
|---|---|---|---|---|
| 5,370,650 | A * | 12/1994 | Tovey | A61B 17/0057 128/899 |
| 5,645,566 | A * | 7/1997 | Brenneman | A61B 17/0057 604/174 |
| 9,138,211 | B2 * | 9/2015 | Whitman | A61B 17/0057 |
| 2004/0009566 | A1 | 1/2004 | Okano et al. | |
| 2008/0086110 | A1 * | 4/2008 | Galdonik | A61M 25/00 604/509 |
| 2009/0093809 | A1 * | 4/2009 | Anderson | A61B 17/0057 606/41 |
| 2011/0094655 | A1 * | 4/2011 | Wiita | A61M 25/0069 156/157 |

FOREIGN PATENT DOCUMENTS

WO    WO 2002/008387    1/2002

* cited by examiner

*Primary Examiner* — Yashita Sharma
(74) *Attorney, Agent, or Firm* — Jason H. Vick; Sheridan Ross, PC (57) ABSTRACT

There is provided a treatment method that is capable of reducing burden on a patient when a medical sheet is indwelled in the body of the patient. A treatment method includes an introduction of introducing a catheter, which has stored a medical sheet (e.g., a myocardial cell sheet), to a heart inside a living body, and an indwelling step of drawing the myocardial cell sheet from the catheter and indwelling the myocardial cell sheet in the heart.

9 Claims, 9 Drawing Sheets

TREATMENT METHOD AND MEDICAL DEVICE

CROSS REFERENCE TO RELATED APPLICATIONS

The present application claims the benefit of priority, under 35 U.S.C. § 119(e), to Japanese Patent Application No. 2016-022256, filed Feb. 8, 2016, entitled "Treatment Method and Medical Device" the entire disclosure of which is incorporated herein by reference, in its entirety, for all that it teaches and for all purposes.

TECHNICAL FIELD

The present invention relates to a treatment method using a medical sheet, and a medical device.

BACKGROUND

In recent years, to improve the pathological condition of severe cardiac insufficiency caused by ischemic heart diseases such as myocardial infarction and angina pectoris, a medical sheet, which is obtained by culturing cells collected from a patient and forming the cells into a sheet shape, is indwelled and transplanted in the heart of the patient.

In a case where a medical sheet is indwelled over a wide area of an organ such as a heart, the medical sheet is formed to have a sufficient size (for example, refer to Japanese Patent Application JP-T-2002-008387).

If a large body surface is incised to follow the shape of a medical sheet when the medical sheet is indwelled in an organ such as a heart, invasiveness into a human body increases, and burden on a patient becomes excessive, which is a problem.

SUMMARY

Problem that is Solved

The embodiments herein are made in light of the problems described above, and an object of the embodiments herein is to provide a treatment method and a medical device which are capable of reducing the burden on a patient when a medical sheet is indwelled in the body.

Solution

To achieve the object, a treatment method of the embodiments herein includes an introduction step of introducing a catheter, which stores a medical sheet, to a target site inside a body, and an indwelling step of drawing the medical sheet from the catheter and indwelling the medical sheet in the target site.

Advantages

In the treatment method, a medical sheet stored in a catheter is introduced to and indwelled in a target site. In this configuration, it is possible to minimally invasively indwell the medical sheet to the target site without incising a large body surface of a patient. Accordingly, if the treatment method is used, it is possible to reduce the burden on the patient when indwelling the medical sheet in the body.

BRIEF DESCRIPTION OF THE DRAWINGS

FIG. 1A is a view illustrating the medical device.

FIGS. 3A&B shows perspective views in which the distal protective cover and the proximal protective cover are detached from the medical device in FIGS. 1A&B; FIG. 3AA is a view illustrating the medical device, and FIG. 3BB is a sectional view of the medical device taken along the axial direction.

FIGS. 4A&B shows perspective views illustrating a state in which support portions and claw portions of a gripping member protrude from a distal portion of a catheter in the medical device illustrated in FIG. 3; FIG. 4AA is a view illustrating the medical device.

DETAILED DESCRIPTION

Hereinafter, the embodiments herein will be described with the accompanying drawings. The same reference signs are assigned to the same configuration elements in the description of the drawings, and duplicated description will be omitted. For illustrative purposes, the size or ratio of each member in the drawings may be exaggerated and may be different from an actual size or ratio. In a medical device 10, a distal side is equivalent to a distal portion 11b side of a catheter 11 introduced into a living body 310, and a proximal side is equivalent to a proximal portion 13a side of a cylindrical body 13 operated by an operator or the like.

First, the medical device 10 used in a treatment method will be described with reference to FIGS. 1A to 4B.

Figure 1A:
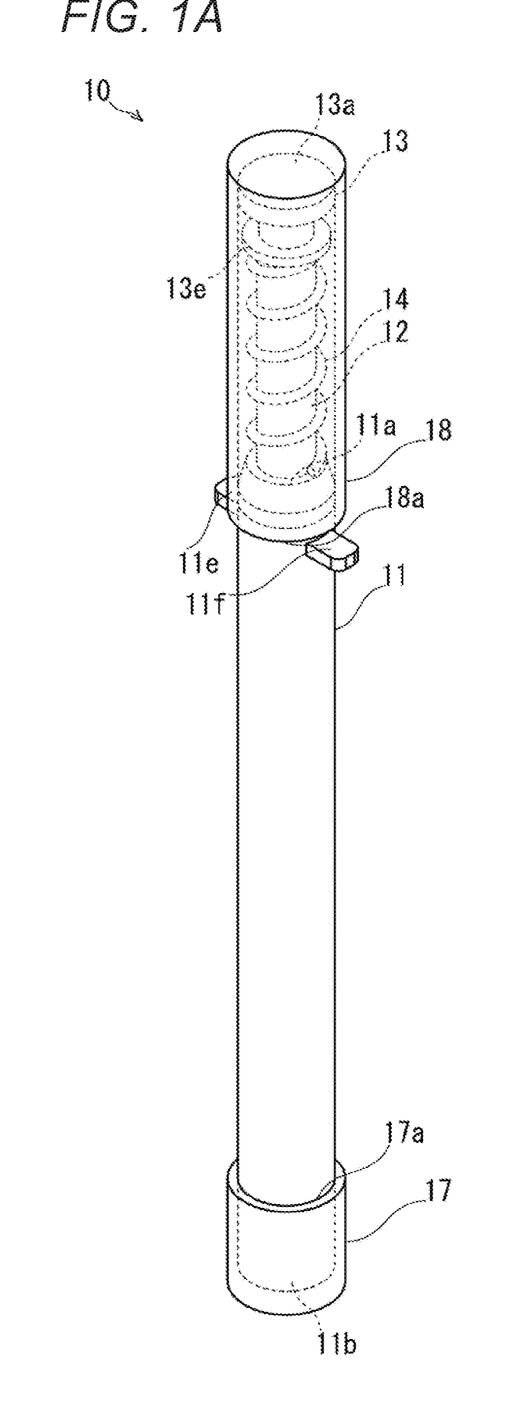
FIGS. 1A&B shows perspective views illustrating the main configuration of a medical device.
Figure 1B:
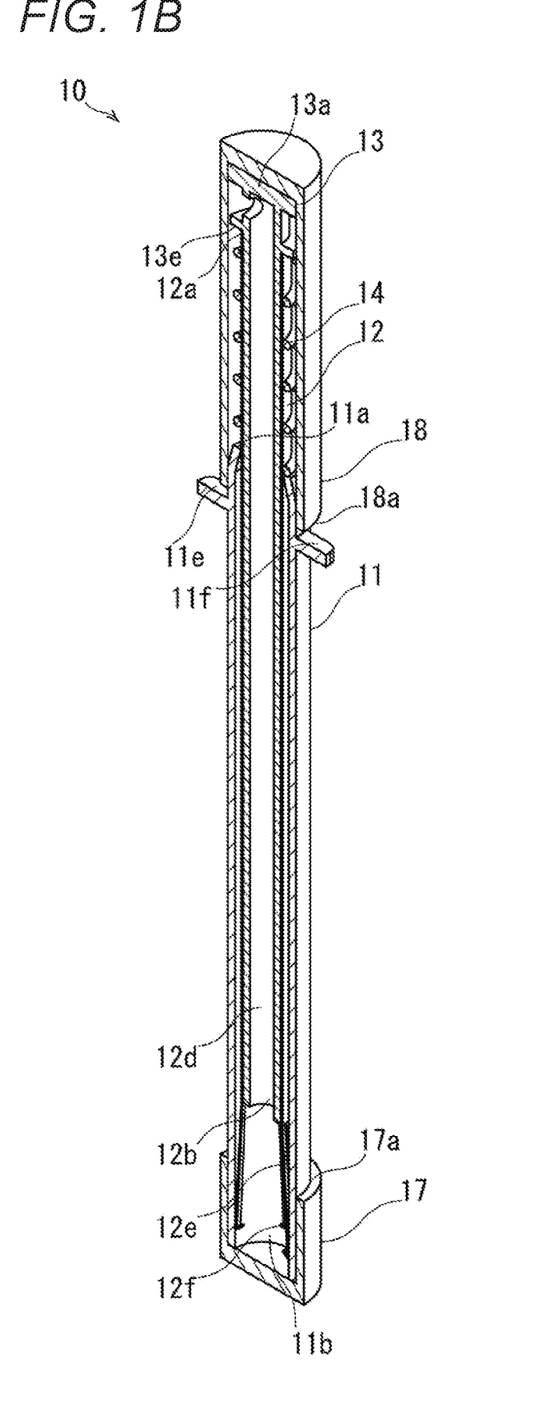
FIG. 1B is a sectional view of the medical device taken along an axial direction.
Figure 2:
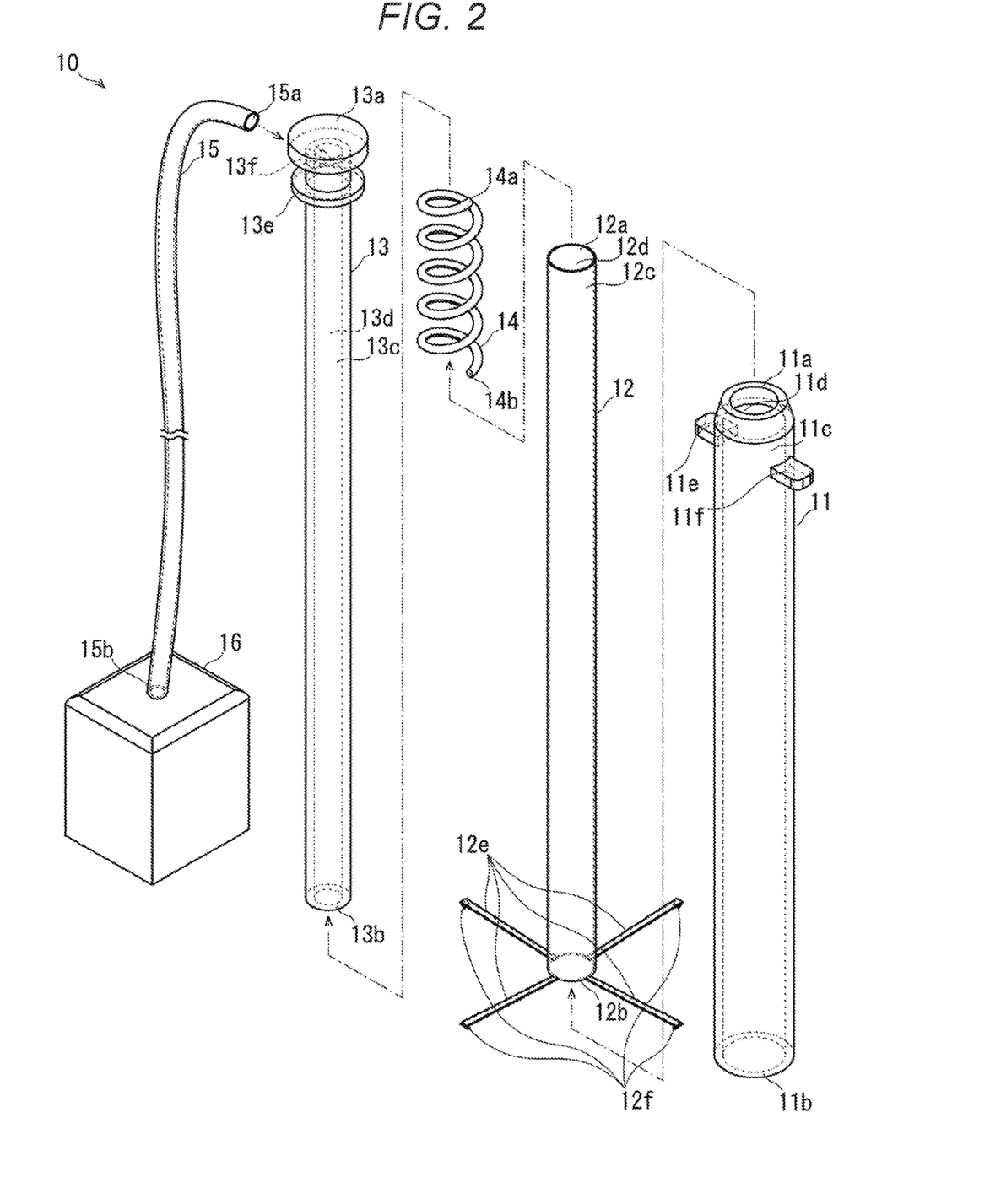
FIG. 2 shows exploded perspective views illustrating a state in which a distal protective cover and a proximal protective cover are detached from the medical device in FIGS. 1A&B, and then an aspiration tube and an aspiration pump are attached to the medical device.
Figure 3A:
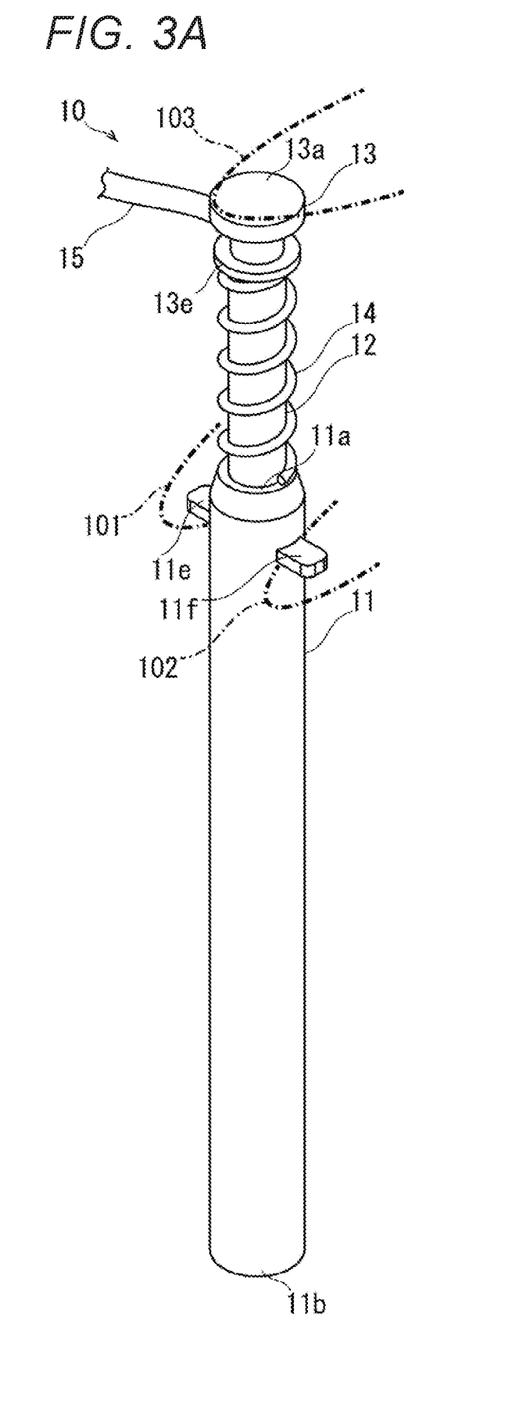
Figure 3B:
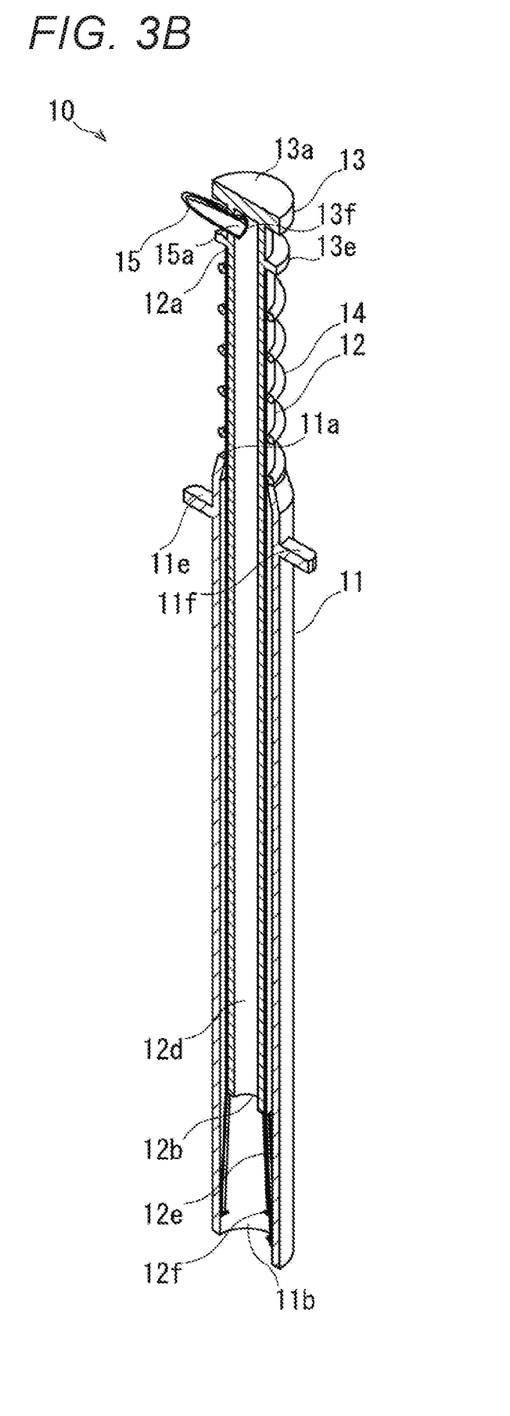
Figure 4A:
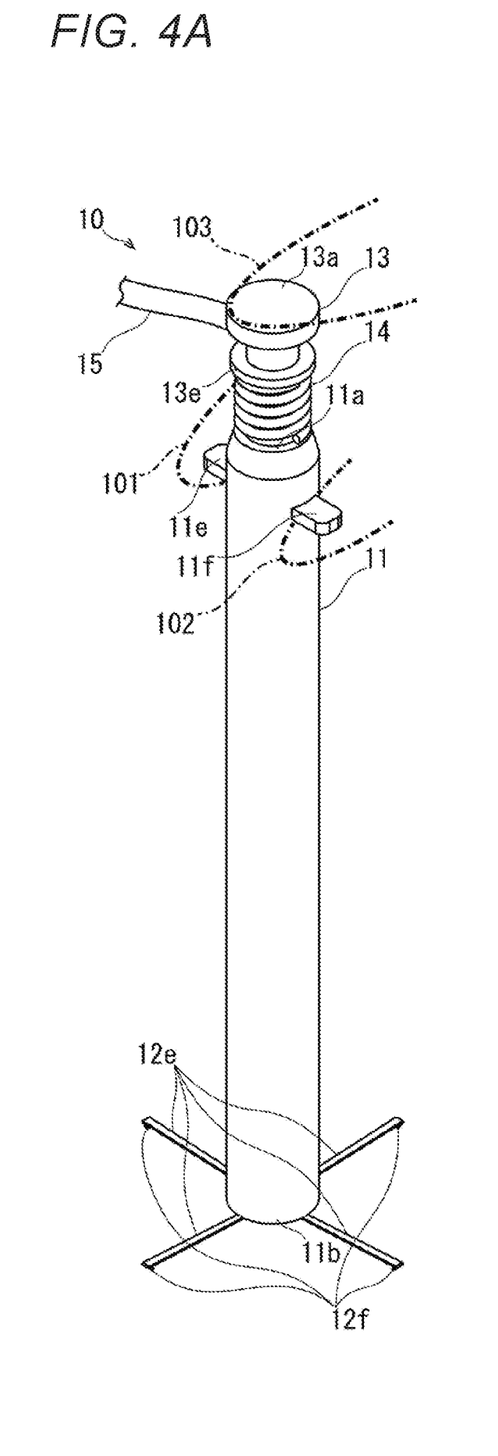
Figure 4B:
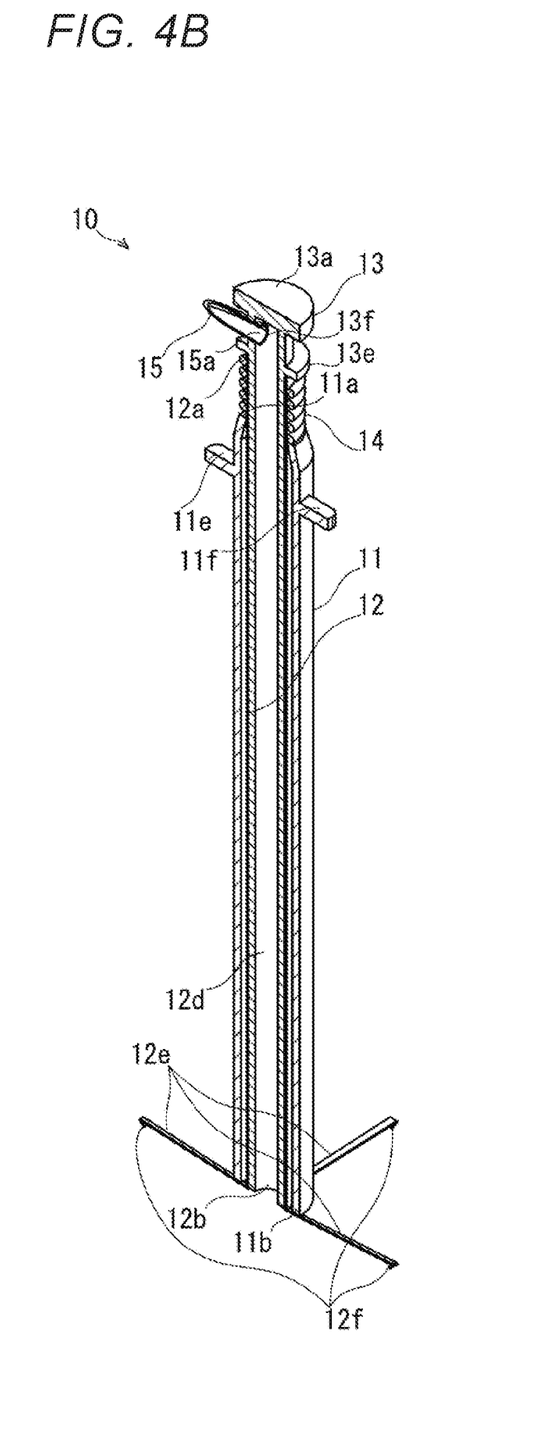
FIG. 4B is a sectional view of the medical device taken along the axial direction.

FIGS. 1A&B show perspective views illustrating a configuration of the medical device 10; FIG. 1A is a view illustrating the medical device 10, and FIG. 1B is a sectional view of the medical device 10 taken along an axial direction. FIG. 2 shows exploded perspective views illustrating a state in which a distal protective cover 17 and a proximal protective cover 18 are detached from the medical device 10 in FIGS. 1A&B, and then an aspiration tube 15 and an aspiration pump 16 are attached to the medical device 10. FIGS. 3A&B show perspective views in which the distal protective cover 17 and the proximal protective cover 18 are detached from the medical device 10 in FIGS. 1A&B; FIG. 3A is a view illustrating the medical device 10, and FIG. 3B is a sectional view of the medical device 10 taken along the axial direction. FIGS. 4A&B show perspective views illustrating a state in which support portions 12e and claw portions 12f of a gripping member 12 protrude from the distal portion 11b of the catheter 11 in the medical device 10 illustrated in FIG. 3; FIG. 4A is a view illustrating the medical device 10, and FIG. 4B is a sectional view of the medical device 10 taken along the axial direction.

As illustrated in FIGS. 1A to 4B, the catheter 11 accommodates a myocardial cell sheet 110, and a proximal side of the catheter 11 serves a hand operation portion operated by the operator or the like.

As illustrated in FIG. 2, the catheter 11 is formed into a cylindrical shape including a lumen 11d. A proximal portion 11a and the distal portion 11b which are respectively positioned at both ends along the axial direction are open. The proximal portion 11a of the catheter 11 is inclined inward toward the proximal side in a radial direction. The inner diameter of the lumen 11d is slightly larger than the diameter of an outer peripheral portion 12c of the gripping member 12 (to be described later) apart from the area of the proximal portion 11a. The inner diameter of the lumen 11d in an edge portion of the proximal portion 11a is slightly larger than the diameter of the outer peripheral portion 12c of the gripping member 12.

As illustrated in FIGS. 3A&B, the gripping member 12 is inserted into the lumen 11d from the distal portion 11b side of the catheter 11. As illustrated in FIG. 2, the catheter 11 includes a first hook 11e in a proximal side area of an outer peripheral portion 11c of the catheter 11, and the first hook 11e has a rectangular shape and protrudes outward in the radial direction. The first hook 11e is a portion onto which the operator or the like hooks a forefinger 101. The catheter 11 includes a second hook 11f facing the first hook 11e in the proximal side area of the outer peripheral portion 11c of the catheter 11. The second hook 11f has the same shape as that of the first hook 11e, and is a portion onto which the operator or the like hooks a middle finger 102.

The catheter 11 may be formed into a straight tubular shape using hard acrylic resin or the like such that the catheter 11 can be easily introduced into a target site even if the catheter 11 is pressed by biological tissues until the target site is reached. In contrast, the catheter 11 may be formed into a bellows shape using resin having flexibility such that the catheter 11 can be easily introduced to a target site even if the target site is a curved site or there is a curved site until the target site is reached. The catheter 11 may be formed of a transparent material for the operator to visually confirm the state of the myocardial cell sheet 110 accommodated inside the lumen 11d.

As illustrated in FIGS. 1A to 4B, the gripping member 12 stores the myocardial cell sheet 110 inside the catheter 11.

As illustrated in FIG. 2, the gripping member 12 is formed into a cylindrical shape having a sufficiently thin thickness between the outer peripheral portion 12c and an inner peripheral portion 12d. A proximal portion 12a and a distal portion 12b which are respectively positioned at both ends along the axial direction are open. Multiple long support portions 12e protrude outward from the distal portion 12b in the radial direction of the gripping member 12. A total of four support portions 12e are formed at intervals of 90° in a circumferential direction along an edge of the distal portion 12b.

As illustrated in FIG. 2, each of the support portions 12e is integrally formed with the distal portion 12b, and is bent from the distal portion 12b outward at a right angle in the radial direction perpendicular to the axial direction. Each of the support portions 12e includes the claw portion 12f that is formed into a claw shape by bending a distal portion of the support portion 12e inward in the radial direction of the gripping member 12. The gripping member 12 may be formed of a shape-memory alloy such as a Nickel-Titanium (Ni—Ti) alloy having superelasticity such that the gripping member 12 is capable of holding the shape even if the gripping member 12 is moved into and out of the catheter 11. For example, the gripping member 12 may be formed of resin having elasticity.

As illustrated in FIGS. 4A&B, if the support portions 12e and the claw portions 12f protrude from the catheter 11, the support portions 12e and the claw portions 12f extend outward in the radial direction of the catheter 11. If the support portions 12e and the claw portions 12f are attached to the myocardial cell sheet 110 in a moist state, the myocardial cell sheet 110 adheres to the support portions 12e and the claw portions 12f. An outer peripheral portion 110b of the myocardial cell sheet 110 is hooked and gripped by the claw portions 12f.

As illustrated in FIGS. 3A&B, the support portions 12e and the claw portions 12f are inserted into the lumen 11d of the catheter 11. The support portions 12e and the claw portions 12f are inserted into the lumen 11d while being deformed inward in the radial direction of the catheter 11 in a state where the support portions 12e and the claw portions 12f grip the myocardial cell sheet 110 (not illustrated in FIG. 3). When the support portions 12e are inserted into the lumen 11d, the support portions 12e are folded in a state where the support portions 12e surround the myocardial cell sheet 110 from the outside. If the support portions 12e and the claw portions 12f protrude from the catheter 11, the support portions 12e and the claw portions 12f extend outward in the radial direction of the catheter 11 again.

As illustrated in FIGS. 1A to 4B, the cylindrical body 13 supports the gripping member 12 from the inside, and a proximal side of the cylindrical body 13 serves as a hand operation portion operated by the operator or the like.

As illustrated in FIG. 2, the cylindrical body 13 is formed into a cylindrical shape including an outer peripheral portion 13c and an inner peripheral portion 13d. The proximal portion 13a along the axial direction is blocked, and a distal portion 13b along the axial direction is open. As illustrated in FIGS. 3A&B, the proximal portion 13a is formed into a circular disc shape such that the proximal portion 13a can be pressed by a thumb 103 of the operator or the like.

As illustrated in FIG. 2, in the cylindrical body 13, a locking portion 13e which locks a spring 14 is formed in a portion of the outer peripheral portion 13c which is positioned in a short distance toward the distal side from the proximal portion 13a. The locking portion 13e is formed into an annular donut shape which protrudes outward from the outer peripheral portion 13c in the radial direction. An air passage portion 13f is formed between the proximal portion 13a and the locking portion 13e in such a way as to pass through the cylindrical body 13 from the outer peripheral portion 13c to the inner peripheral portion 13d. The air passage portion 13f is a hole into which one end portion 15a of the aspiration tube 15 (to be described later) is inserted.

As illustrated in FIGS. 3A&B, the cylindrical body 13 is inserted into the gripping member 12. The proximal portion 12a of the gripping member 12 is attached to the locking portion 13e of the cylindrical body 13. The position of the distal portion 13b of the cylindrical body 13 coincides with the position of the distal portion 12b of the gripping member 12. The cylindrical body 13 is joined to a portion of the gripping member 12 from the proximal portion 12a to the distal portion 12b via an adhesive or the like, and the cylindrical portion supports that portion from the inside.

To maintain the negative pressure (reduced pressure) state of the inner peripheral portion 13d after the inner peripheral portion 13d has been aspirated by the aspiration pump 16 and the pressure of the inner peripheral portion 13d has become negative, the cylindrical body 13 may have air tightness between the distal protective cover 17 (to be described later) and the catheter 11, and a check valve may be provided in the air passage portion 13f.

Similar to the catheter 11, the cylindrical body 13 may be formed into a straight tubular shape using hard acrylic resin or the like such that the cylindrical body 13 can be easily introduced into a target site even if the cylindrical body 13 is pressed by biological tissues until the target site is reached. In contrast, similar to the catheter 11, the cylindrical body 13 may be formed into a bellows shape using resin having flexibility such that the cylindrical body 13 can be easily introduced to a target site even if the target site is a curved site or there is a curved site until the target site is reached.

As illustrated in FIGS. 1A to 4B, the spring 14 acts to insert a distal side of the gripping member 12 into the catheter 11.

The spring 14 can have a spirally wound shape. If the spring 14 is pressed, the spring 14 is contracted in the axial direction, and if the pressurizing of the spring 14 is released, the spring 14 returns to its original length along the axial direction. The inner diameter of the spring 14 is slightly larger than the diameter of the outer peripheral portion 12c of the gripping member 12. For example, the spring 14 is formed of stainless steel for spring. As illustrated in FIGS. 3A&B, the gripping member 12 is inserted through the catheter 11 from the distal portion 11b side. In this state, the spring 14 is inserted through the gripping member 12 from a proximal portion 12a side. The cylindrical body 13 is inserted through the gripping member 12 from the proximal portion 12a side. As a result, one end portion 14a of the spring 14 is attached to the locking portion 13e of the cylindrical body 13, and the other end portion 14b is attached to the edge of the proximal portion 11a of the catheter 11.

As illustrated in FIG. 4A, in a state where the forefinger 101 is hooked onto the first hook 11e of the catheter 11, and the middle finger 102 is hooked onto the second hook 11f of the catheter 11, the proximal portion 13a of the cylindrical body 13 is pressed by the thumb 103. As a result, the spring 14 is contracted, and the claw portions 12f and the support portions 12e of the gripping member 12 protrude from the distal portion 11b of the catheter 11.

In contrast, if the force of the thumb 103 which presses the proximal portion 13a of the cylindrical body 13 is gradually reduced in a state illustrated in FIG. 4A, the spring 14 extends and comes into a state illustrated in FIG. 3B. As a result, the claw portions 12f and the support portions 12e of the gripping member 12 are inserted into the distal portion 11b of the catheter 11.

As illustrated in FIGS. 2 to 4B, the cylindrical body 13 and the aspiration pump 16 communicate to each other via the aspiration tube 15.

The aspiration tube 15 is formed into an elongated cylindrical shape having plasticity. The aspiration tube 15 is formed of a soft material, for example polyolefin resin. The one end portion 15a of the aspiration tube 15 is inserted into the air passage portion 13f of the cylindrical body 13, and the other end portion 15b is connected to the aspiration pump 16. The aspiration tube 15 has a sufficient length such that the operator can easily handle the medical device 10 in an operation room.

As illustrated in FIG. 2, the aspiration pump 16 aspirates the myocardial cell sheet 110, which is gripped by the gripping member 12, into the catheter 11.

The aspiration pump 16 is a well-known vacuum pump, and for example, a simple oilless type is used. The aspiration pump 16 aspirates the myocardial cell sheet 110 from the distal portion 11b of the catheter 11 by reducing the inner pressure of the catheter 11, which communicates to the gripping member 12, via the aspiration tube 15. A power source for the aspiration pump 16 is turned on and off via a foot pedal switch or the like that can be easily handled by the operator. An electrical sensor may be provided between the catheter 11 and the cylindrical body 13, and the power source for the aspiration pump 16 may be automatically turned on while the proximal portion 13a of the cylindrical body 13 is moved away from the proximal portion 11a of the catheter 11. When the distal portion 13b of the cylindrical body 13 is moved away from the proximal portion 11a of the catheter 11, the claw portions 12f of the gripping member 12 are inserted into the catheter 11.

As illustrated in FIGS. 1A&B, the distal protective cover 17 prevents the myocardial cell sheet 110 from becoming dried by sealing and protecting the distal portion 11b of the catheter 11 storing the myocardial cell sheet 110.

The distal protective cover 17 is formed into a cylindrical shape, and a side of the distal protective cover 17 opposite to an opening portion 17a along the axial direction is blocked. An inner peripheral surface of the distal protective cover 17 has a shape following the outer peripheral portion 11c on a distal side of the catheter 11. The distal protective cover 17 is formed of a hard material such as acrylic resin. A worker in a manufacturing line (culture room) of the myocardial cell sheet 110 attaches the distal protective cover 17 to the distal portion 11b of the catheter 11. The distal protective cover 17 is detached from the catheter 11 in an operation room of a medical institution by an operator.

As illustrated in FIGS. 1A&B, the proximal protective cover 18 prevents the myocardial cell sheet 110 from becoming dried by sealing and protecting the proximal side of the medical device 10 which is equivalent to a hand operation portion.

The proximal protective cover 18 is formed into a cylindrical shape, and a side of the proximal protective cover 18 opposite to an opening portion 18*a* along the axial direction is blocked. The proximal protective cover 18 has a shape and is formed of a material which are the same as those of the distal protective cover 17. The proximal protective cover 18 is longer than the distal protective cover 17 along the axial direction. After the worker in the manufacturing line (culture room) of the myocardial cell sheet 110 inserts the distal portion 13*b* and the locking portion 13*e* of the cylindrical body 13 through the proximal protective cover 18, the worker attaches the proximal protective cover 18 to the proximal portion 11*a* of the catheter 11. The proximal protective cover 18 is detached from the catheter 11 and the cylindrical body 13 in the operation room of the medical institution by the operator.

Hereinafter, a treatment method (for example, the indwelling of the myocardial cell sheet 110 in a heart 320) using the medical device 10 will be described with reference to FIG. 5 and FIGS. 6A to 6I.

Figure 5:
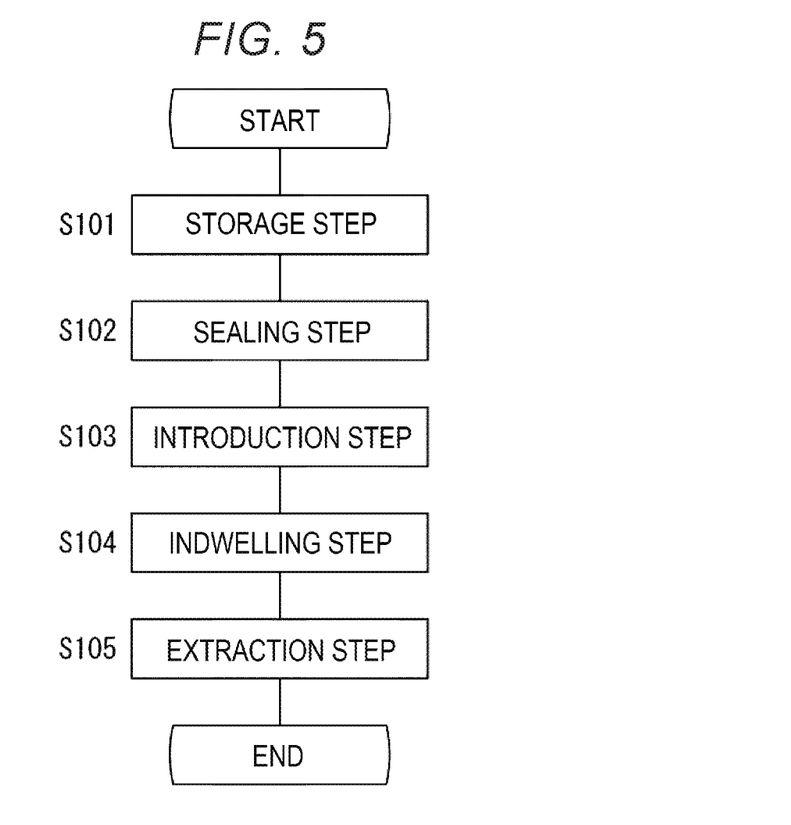
FIG. 5 is a flowchart illustrating a sequence of a treatment method using the medical device.

FIG. 5 is a flowchart illustrating a sequence of the treatment method using the medical device 10. FIGS. 6A to 6I are schematic views illustrating the sequence of the treatment method using the medical device 10.

A storage step S101 (FIG. 5) is a step of storing the myocardial cell sheet 110 in the distal portion 11*b* of the catheter 11 while gripping the myocardial cell sheet 110, and corresponds to steps illustrated in FIGS. 6A to 6E.

Figure 6A:
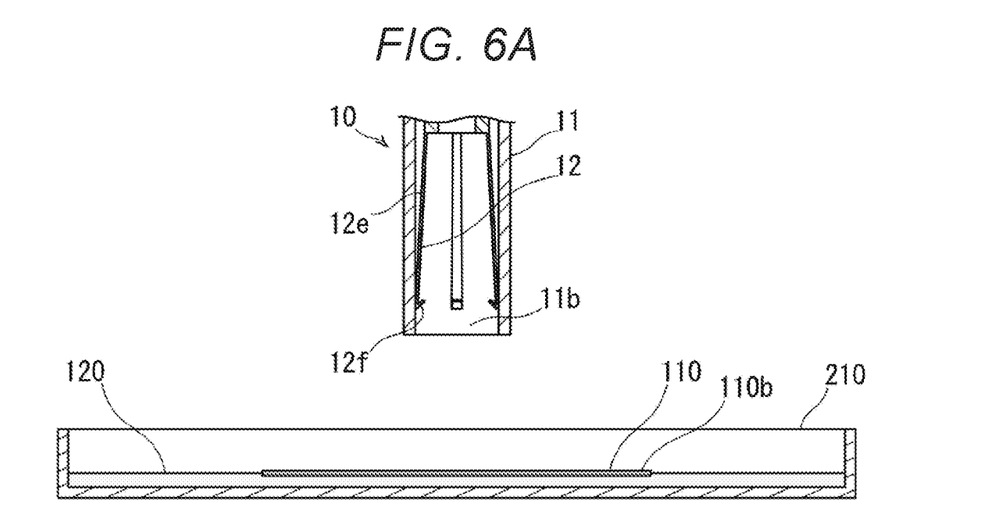
FIG. 6A is a schematic view illustrating the sequence of the treatment method using the medical device, and is a view illustrating a state in which the support portions and the claw portions of the gripping member are inserted into the distal portion of the catheter.

As illustrated in FIG. 6A, a worker (not illustrated here and hereinafter) in a manufacturing line (culture room) of the myocardial cell sheet 110 brings the distal side of the medical device 10 close to a Schale 210 (e.g., a laboratory dish) that stores the myocardial cell sheet 110 in a state of being submerged in a culture solution 120. The myocardial cell sheet 110 is formed into a circular shape having a thin thickness. At this time, the claw portions 12*f* and the support portions 12*e* of the gripping member 12 are in a state of being inserted into the distal portion 11*b* of the catheter 11.

Figure 6B:
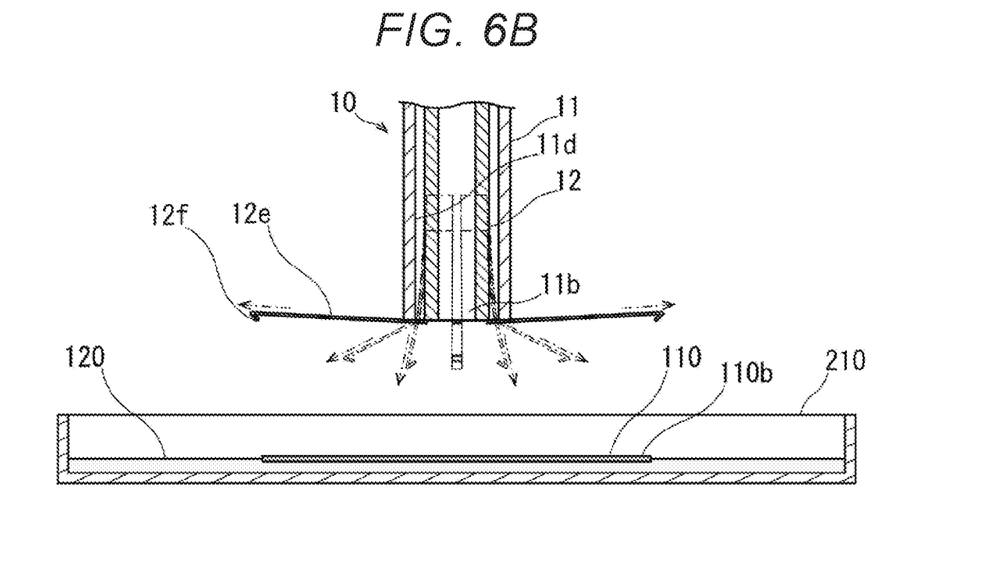
FIG. 6B is a view illustrating in a stepwise manner a state in which the support portions and the claw portions of the gripping member protrude from the distal portion of the catheter, which is subsequent to the state in FIG. 6A.

As illustrated in FIG. 6B, the worker causes the claw portions 12*f* and the support portions 12*e* of the gripping member 12 to protrude from the distal portion 11*b* of the catheter 11. That is, as illustrated in FIG. 4A, the worker presses the proximal portion 13*a* of the cylindrical body 13 with the thumb 103 in a state where the forefinger 101 is hooked onto the first hook 11*e* of the catheter 11 and the middle finger 102 is hooked onto the second hook 11*f* of the catheter 11.

As illustrated by multiple dotted lines and solid lines in FIG. 6B, the claw portions 12*f* and the support portions 12*e* of the gripping member 12 are extruded outward while being rubbed against an end portion of the lumen 11*d* of the catheter 11. A portion of each of the support portions 12*e* which has protruded outward from the distal portion 11*b* of the catheter 11 extends outward in the radial direction of the catheter 11. In a state where each of the support portions 12*e* has fully protruded from the distal portion 11*b* of the catheter 11, the support portion 12*e* extends in a direction substantially perpendicular to the axial direction of the catheter. Since the claw portion 12*f* is provided at a distal end of the support portion 12*e*, the claw portion 12*f* is positioned on an outermost distal side in the radial direction of the catheter 11.

Figure 6C:
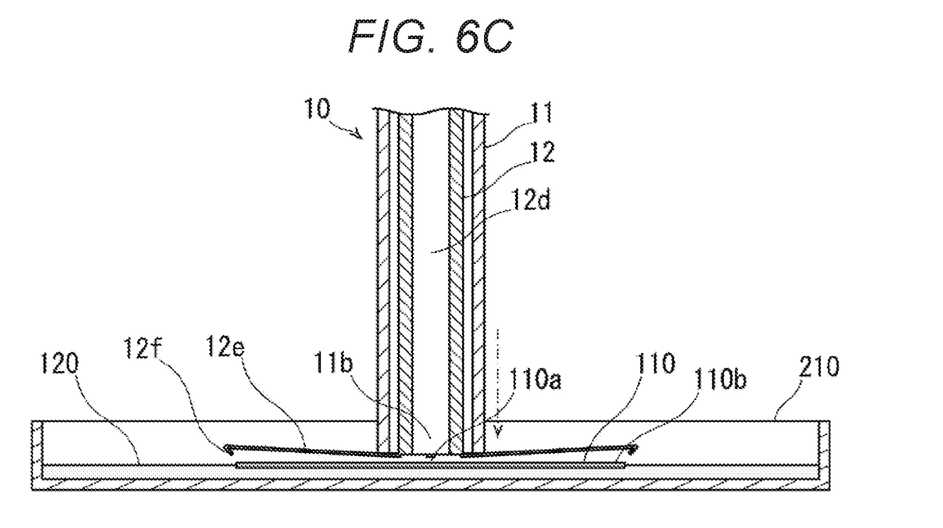
FIG. 6C is a view illustrating a state in which the support portions and the claw portions of the gripping member are set to face a myocardial cell sheet stored in a Schale, which is subsequent to the state in FIG. 6B.

As illustrated in FIG. 6C, the claw portions 12*f* of the gripping member 12 are set to face the outer peripheral portion 110*b* of the myocardial cell sheet 110 that is stored in the Schale 210 in a state where the myocardial cell sheet 110 is submerged in the culture solution 120. Thereafter, the worker attaches the support portions 12*e* and the claw portions 12*f* to the myocardial cell sheet 110. Since the myocardial cell sheet 110 is in a state of being submerged in the culture solution 120, if the support portions 12*e* and the claw portions 12*f* are attached to the myocardial cell sheet 110, the myocardial cell sheet 110 adheres to the support portions 12*e* and the claw portions 12*f*.

Figure 6D:
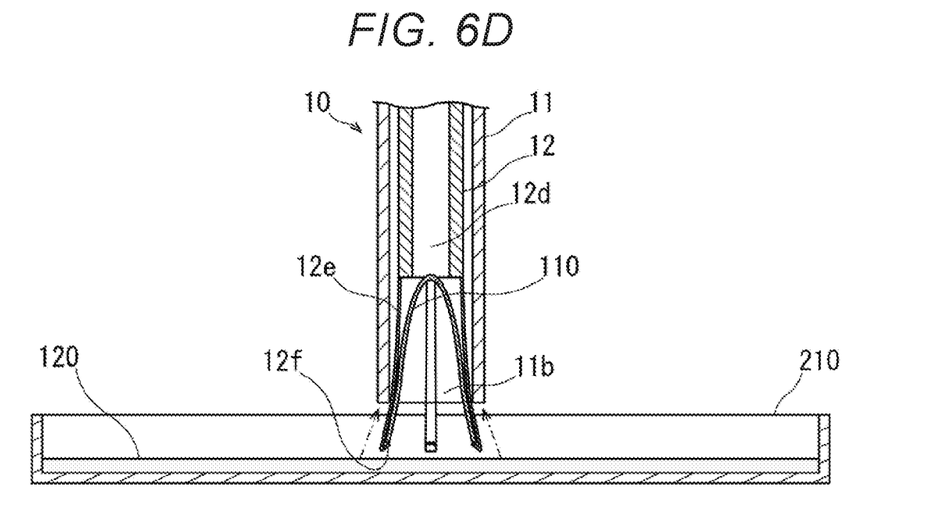
FIG. 6D is a view illustrating a state in which the insertion of the support portions and the claw portions of the gripping member gripping the myocardial cell sheet into the distal portion of the catheter is in progress, which is subsequent to the state in FIG. 6C.
Figure 6E:
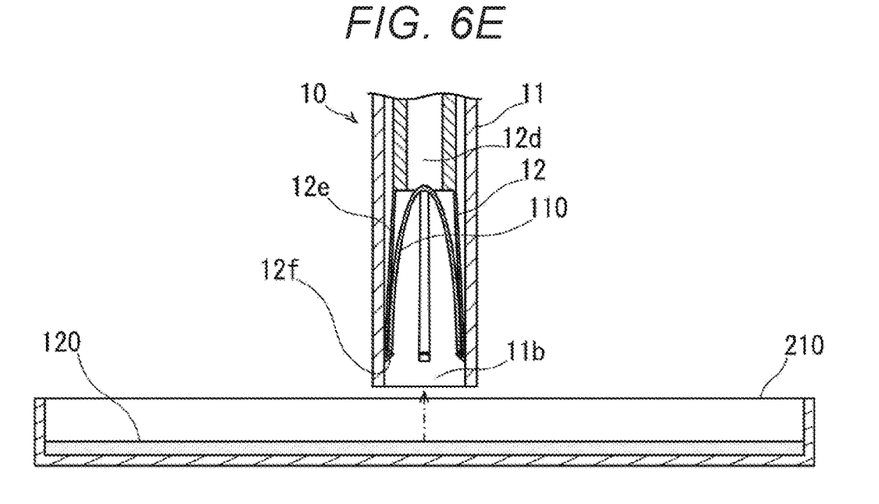
FIG. 6E is a view illustrating a state in which the insertion of the support portions and the claw portions of the gripping member gripping the myocardial cell sheet into the distal portion of the catheter is complete, which is subsequent to the state in FIG. 6D.

As illustrated in FIGS. 6D and 6E, the worker inserts the myocardial cell sheet 110 into the distal portion 11*b* of the catheter 11. That is, if the worker gradually reduces the force of the thumb 103 which presses the proximal portion 13*a* of the cylindrical body 13 in the state illustrated in FIG. 4A, the medical device 10 is brought into the state illustrated in FIG. 3B. At the same time, the worker aspirates a central portion 110*a* of the myocardial cell sheet 110 using the aspiration pump 16. As a result, the claw portions 12*f* of the gripping member 12 are inserted into the distal portion 11*b* of the catheter 11 while gripping the outer peripheral portion 110*b* of the myocardial cell sheet 110. The myocardial cell sheet 110 is folded while being surrounded by the four support portions 12*e* of the gripping member 12.

A sealing step S102 (FIG. 5) is a step of sealing the distal portion 11*b* of the catheter 11 and the like which is subsequent to the storage step S101. The sealing step S102 corresponds to a step illustrated in FIG. 6F.

Figure 6F:
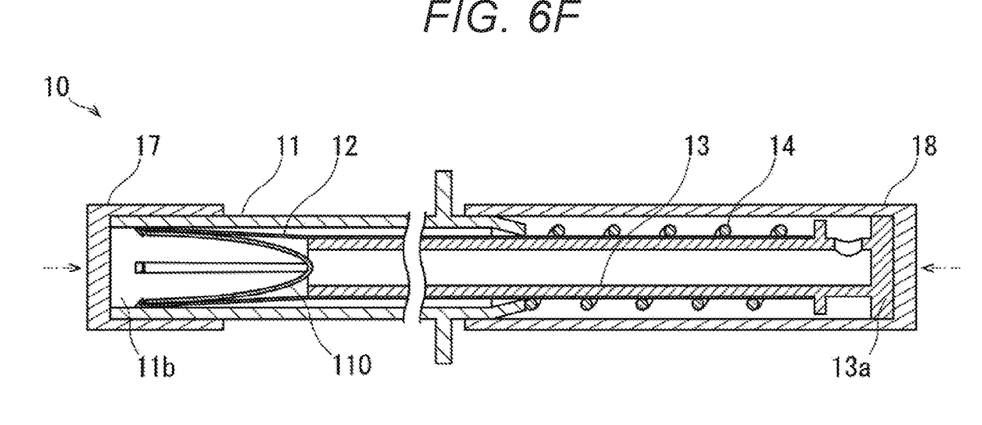
FIG. 6F is a view illustrating a state in which the distal protective cover is attached to the distal portion of the catheter, and the proximal protective cover is attached to a cylindrical body, which is subsequent to the state in FIG. 6E.

As illustrated in FIG. 6F, the worker attaches the distal protective cover 17 to the distal portion 11*b* of the catheter 11 which is equivalent to the distal side of the medical device 10. The worker attaches the proximal protective cover 18 to a portion of the cylindrical body 13 and the catheter 11 which are positioned on the proximal side of the medical device 10. In virtue of the sealing step S102, the myocardial cell sheet 110 manufactured in the manufacturing line (culture room) is transported to an operation room of a medical institution in a state where the myocardial cell sheet 110 is stored in the medical device 10.

An introduction step S103 (FIG. 5) is a step of introducing the catheter 11, which has stored the myocardial cell sheet 110 in the distal portion 11*b*, to the heart 320 inside the living body 310 which is subsequent to the sealing step S102. The introduction step S103 corresponds to a step illustrated in FIG. 6G.

Figure 6G:
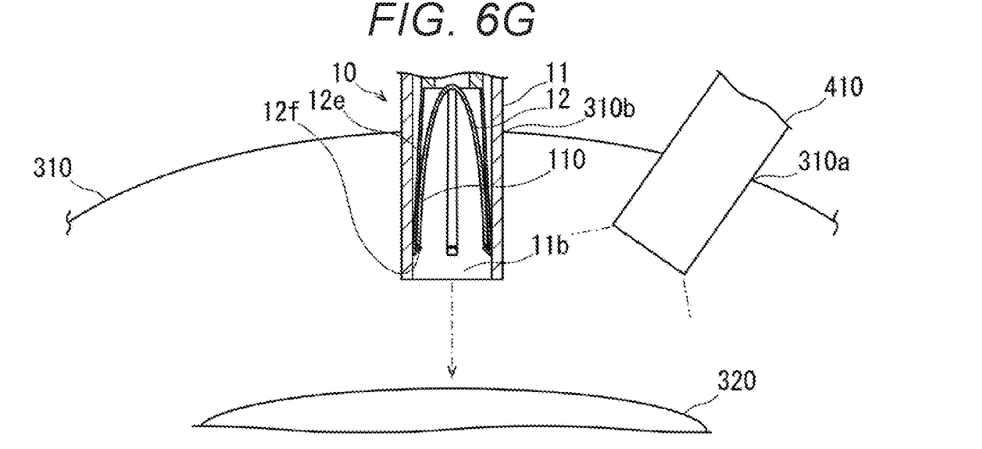
FIG. 6G is a view illustrating a state in which the medical device is inserted into the body of a patient via thoracoscopy and the medical device is set to face the heart, which is subsequent to the state in FIG. 6F.

As illustrated in FIG. 6G, an operator (not illustrated here and hereinafter) detaches the distal protective cover 17 and the proximal protective cover 18 from the medical device 10, and introduces the distal side of the medical device 10 to the heart 320 inside the living body 310. That is, after the operator inserts an imaging camera 410 into an opening 310*a* that is incised in advance, the operator introduces the medical device 10 to the heart 320 from another opening 310*b*, which is incised in advance, via thoracoscopy. The operator sets the distal side of the medical device 10 (the distal portion 11*b* of the catheter 11) to face the heart 320.

An indwelling step S104 (FIG. 5) is a step of pushing the myocardial cell sheet 110 from the distal portion 11*b* of the catheter 11, and indwelling the myocardial cell sheet 110 in the heart 320 which is subsequent to the introduction step S103. The indwelling step S104 corresponds to a steps illustrated in FIGS. 6H and 6I.

Figure 6H:
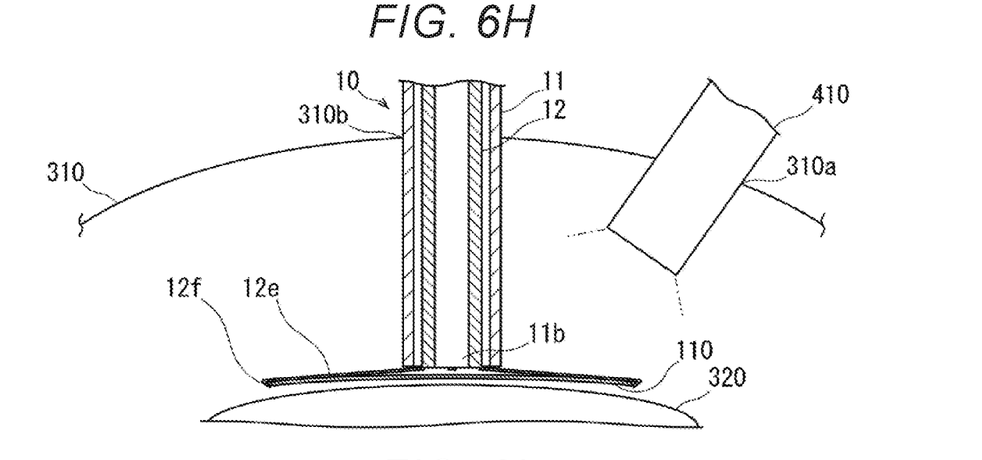
FIG. 6H is a view illustrating a state in which the support portions and the claw portions of the gripping member gripping the myocardial cell sheet protrude from the distal portion of the catheter and the myocardial cell sheet is set to face the heart, which is subsequent to the state in FIG. 6G.

As illustrated in FIG. 6H, the operator causes the claw portions 12*f* and the support portions 12*e* of the gripping member 12, which grip the myocardial cell sheet 110, to protrude from the distal portion 11*b* of the catheter 11 via thoracoscopy. That is, as in the state illustrated in FIG. 4A, the operator presses the proximal portion 13*a* of the cylindrical body 13 with the thumb 103 in a state where the forefinger 101 is hooked onto the first hook 11*e* of the catheter 11 and the middle finger 102 is hooked onto the second hook 11f of the catheter 11. The operator sets the myocardial cell sheet 110, which has protruded from the distal portion 11b of the catheter 11, to face the heart 320.

Figure 6I:
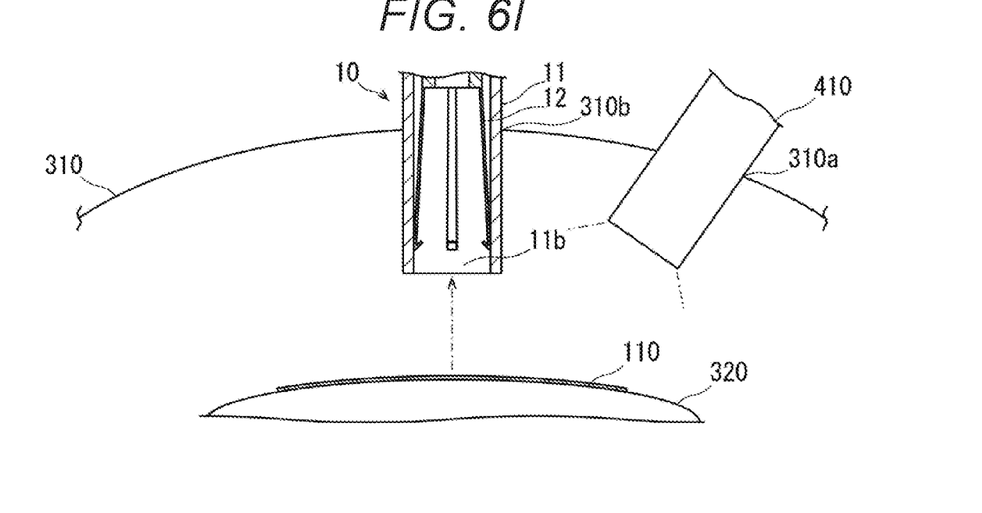
FIG. 6I is a view illustrating a state in which the myocardial cell sheet is indwelled in the heart, which is subsequent the state in FIG. 6H.

As illustrated in FIG. 6I, the operator indwells the myocardial cell sheet 110, which is gripped by the gripping member 12, in the heart 320. Since the myocardial cell sheet 110 is moist, if the myocardial cell sheet 110 is attached to the heart 320, the myocardial cell sheet 110 adheres thereto.

An extraction step S105 (FIG. 5) is a step of extracting the medical device 10 and the imaging camera 410 to the outside of the living body 310 which is subsequent to the indwelling step S104.

The operator extracts the medical device 10 from the opening 310b of the living body 310 to the outside. Thereafter, the operator extracts the imaging camera 410 from the opening 310a of the living body 310 to the outside. The operator completes an operation by closing the opening 310a and the opening 310b.

According to the following configuration of the treatment method and the medical device 10, operational effects are obtained.

The treatment method includes the introduction step S103 of introducing the catheter 11, which has stored a medical sheet (the myocardial cell sheet 110), to a target site (the heart 320) inside a body (the living body 310), and the indwelling step S104 of drawing the myocardial cell sheet 110 from the catheter 11 and indwelling the myocardial cell sheet 110 in the heart 320.

The medical device 10 of the embodiment includes the catheter 11 including the lumen 11d that accommodates the myocardial cell sheet 110, and the gripping member 12 that stores the myocardial cell sheet 110 in the lumen 11d by gripping the myocardial cell sheet 110 and being inserted into the lumen 11d.

According to the treatment method and the medical device 10, the myocardial cell sheet 110, which is stored in the catheter 11, is introduced to and indwelled in the heart 320 inside the living body 310. In the configuration, it is possible to minimally invasively indwell the myocardial cell sheet 110 in the heart 320 without incising a large body surface of a patient. Accordingly, if the treatment method and the medical device 10 are used, it is possible to reduce burden on the patient when indwelling the myocardial cell sheet 110 in the living body 310.

The treatment method includes the storage step S101 of storing the myocardial cell sheet 110 in the catheter 11 while gripping the myocardial cell sheet 110, and the sealing step S102 of sealing the catheter 11. In the introduction step S103, after the sealing of the catheter 11 is released, the catheter 11 is introduced to the heart 320.

According to the treatment method, since the myocardial cell sheet 110 manufactured in a manufacturing line (culture room) is hygienically stored in the catheter 11, it is possible to collectively manage the quality of the myocardial cell sheet 110 until the myocardial cell sheet 110 is transported to an operation room of a medical institution.

In the storage step S101 of the treatment method, the myocardial cell sheet 110 is stored in the catheter 11 while the central portion 110a of the myocardial cell sheet 110 is aspirated.

The medical device 10 includes the aspiration pump 16 that aspirates the myocardial cell sheet 110 gripped by the gripping member 12.

According to the treatment method and the medical device 10, it is possible to more reliably store the myocardial cell sheet 110 in the catheter 11 by aspirating the myocardial cell sheet 110 into the catheter 11.

In the storage step S101 of the treatment method, the myocardial cell sheet 110 is stored in the catheter 11 while the outer peripheral portion 110b of the myocardial cell sheet 110 is gripped.

In the medical device 10, the claw portions 12f grip the outer peripheral portion 110b of the myocardial cell sheet 110.

According to the treatment method and the medical device 10, it is possible to reliably store the entirety of the myocardial cell sheet 110 in the catheter 11 by forcibly loading the entirety of the myocardial cell sheet 110 into the catheter 11.

In the treatment method, the myocardial cell sheet 110 is used as a medical sheet, and a target site is the heart 320.

According to the treatment method, it is possible to minimally invasively indwell the myocardial cell sheet 110 in the heart 320 without incising a large body surface of a patient via thoracotomy. Accordingly, it is possible to reduce burden on the patient when indwelling the myocardial cell sheet 110 in the living body 310.

In the introduction step S103 and/or the indwelling step S104 of the treatment method, the catheter 11 is introduced to the heart 320 via thoracoscopy.

According to the treatment method, an operator can safely introduce the catheter 11 to the heart 320 while visually confirming the catheter 11 via thoracoscopy.

In the medical device 10, the gripping member 12 is inserted into the lumen 11d while being deformed inward in the radial direction of the catheter 11.

In the medical device 10, it is possible to smoothly store the myocardial cell sheet 110 in the catheter 11 without applying an excessive load to the myocardial cell sheet 110 gripped by the gripping member 12.

In the medical device 10, the gripping member 12 includes multiple claw portions 12f which are bent at a distal end of the gripping member 12. If the claw portions 12f protrude from the catheter 11, the claw portions 12f extend outward in the radial direction of the catheter 11.

In the medical device 10, when the catheter 11 is set to face the myocardial cell sheet 110, the claw portions 12f easily grip the outer peripheral portion 110b of the myocardial cell sheet 110. Accordingly, the medical device 10 is capable of more reliably storing the myocardial cell sheet 110 in the catheter 11.

Embodiments herein are described above as examples for explanation purposes. The scope of the embodiments herein are not intended to be limited to those embodiments described above. Accordingly, the embodiments herein can be realized in various forms different from the embodiments described above as the various forms do not depart from the concept of the present invention. That is, the embodiments herein can be modified in various forms based on the configuration described in the claims, and the various modifications fall under the category of the present invention.

The treatment method is configured such that the catheter 11 is introduced to the heart 320 via thoracoscopy; however, the embodiments herein are not limited to that configuration. For example, the catheter 11 may be introduced to a predetermined target site (for example, a bowel) via thoracoscopy or another method.

In the treatment method of the embodiment, the myocardial cell sheet 110 is used as a medical sheet; however, the embodiments herein are not limited to that configuration. A medical sheet can be widely applied in such a way as to be indwelled in or joined to an organ inside the living body 310.

A medical sheet is not limited to a configuration in which the medical sheet is permanently indwelled in or joined to an organ inside the living body 310. A medical sheet may be temporarily indwelled.

In the storage step S101 of the treatment method, the myocardial cell sheet 110 is stored in the catheter 11 while the central portion 110a of the myocardial cell sheet 110 is aspirated. In the indwelling step S104, the myocardial cell sheet 110 may be discharged in the storage step S101, and may be drawn from the catheter 11 and indwelled in the heart 320 using the force of discharge.

The medical device 10 is configured such that the myocardial cell sheet 110 is introduced to the heart 320 in a state where the myocardial cell sheet 110 is stored in the distal portion 11b of the catheter 11 however, the embodiments herein are not limited to that configuration. For example, the myocardial cell sheet 110 may be stored in a central portion or the proximal portion 11a of the catheter 11.

The medical device 10 is configured such that when external force is not applied, the gripping member 12 is inserted into the catheter 11 by the extension force of the spring 14; however, the embodiments herein are not limited to that configuration. For example, in a state where the outer peripheral portion 11c of the catheter 11 is gripped with a left hand, a right hand may slide the cylindrical body 13 in the axial direction of the catheter 11 without using the spring 14. In this configuration, if the cylindrical body 13 is pressed toward the distal portion 11b side of the catheter 11, the support portions 12e and the claw portions 12f of the gripping member 12 protrude to the outside of the catheter 11. In contrast, if the cylindrical body 13 is pulled toward a proximal portion 11a side of the catheter 11, the support portions 12e and the claw portions 12f of the gripping member 12 are accommodated in the catheter 11.

The medical device 10 is configured such that the outer peripheral portion 110b of the myocardial cell sheet 110 is hooked and gripped by the four claw portions 12f protruding from the distal portion 12b of the gripping member 12; however, the embodiments herein are not limited to that configuration. For example, the number of claw portions 12f may be two or more. The claw portions 12f are not mandatorily required, and a configuration may be adopted in which the support portions 12e are attached to the myocardial cell sheet 110 and the moist myocardial cell sheet 110 adheres to the support portions 12e. A configuration may be adopted in which the support portions 12e and the claw portions 12f are not provided, and after the myocardial cell sheet 110 is aspirated from the distal portion 12b of the gripping member 12 and is stored in the catheter 11, the myocardial cell sheet 110 is discharged to and indwelled in the heart 320.

DESCRIPTION OF REFERENCE NUMERALS AND SIGNS

10 MEDICAL DEVICE
11 CATHETER
11d LUMEN
12 GRIPPING MEMBER
12e SUPPORT PORTION
12f CLAW PORTION
13 CYLINDRICAL BODY
14 SPRING
15 ASPIRATION TUBE
16 ASPIRATION PUMP (ASPIRATION MEMBER)
17 DISTAL PROTECTIVE COVER
18 PROXIMAL PROTECTIVE COVER
110 MYOCARDIAL CELL SHEET (MEDICAL SHEET)
110a CENTRAL PORTION
110b OUTER PERIPHERAL PORTION
310 LIVING BODY (BODY)
320 HEART (TARGET SITE)

What is claimed is:

1. A treatment method comprising:
   storing a medical sheet inside a lumen of a catheter, wherein during storing of the medical sheet, a negative pressure is maintained inside the lumen of the catheter by applying a vacuum thereto aspirating a central portion of the medical sheet and maintaining the medical sheet in a folded state inside the lumen of the catheter;
   introducing the catheter, which stores the medical sheet therein, to a target site inside a body, wherein the medical sheet is held by a plurality of support portions disposed inside the lumen of the catheter, wherein the plurality of support portions comprise claw portions disposed at an end thereof, wherein the claw portions are bent in a direction radially inward toward an axis of the lumen, and wherein the claw portions extend past and grip an outer peripheral edge of the medical sheet;
   extending the plurality of support portions from the lumen of the catheter, wherein the plurality of support portions extend radially outward from the lumen expanding the medical sheet while being gripped at the outer peripheral edge by the claw portions and disposing the medical sheet in a position outside of the lumen of the catheter;
   indwelling the medical sheet in the target site; and
   extracting the catheter from the body, the medical sheet caused to remain indwelled in the target site inside the body after the catheter has been extracted from the body.

2. The treatment method according to claim 1, wherein prior to introducing the catheter to the target site inside the body, the method further comprises:
   sealing the catheter storing the medical sheet therein with a protective cover disposed at an end of the catheter; and
   releasing the sealing of the catheter by removing the protective cover from the end of the catheter before introducing the catheter to the target site.

3. The treatment method according to claim 1, wherein, during storing of the medical sheet, the plurality of support portions surround the medical sheet in the folded state.

4. The treatment method according to claim 3, wherein a myocardial cell sheet is used as the medical sheet, and the target site is a heart.

5. The treatment method according to claim 4, wherein the catheter is introduced to the target site via thoracoscopy.

6. A medical device comprising:
   a catheter including a lumen that accommodates a medical sheet;
   an aspiration member that maintains a negative pressure in the inside the lumen and aspirates a central portion of the medical sheet gripped by the gripping member and maintains the medical sheet in a folded state inside the lumen of the catheter;
   a gripping member comprising a plurality of support portions disposed inside the lumen of the catheter in an inserted state, wherein the plurality of support portions comprise claw portions disposed at an end thereof, wherein the claw portions are bent in a direction radially inward toward an axis of the lumen, wherein the medical sheet is stored in the lumen by the claw portions extending past and gripping an outer peripheral edge of the medical sheet, wherein the plurality of support portions extend radially outward from the lumen of the catheter in a protruded state expanding the medical sheet while being gripped at the outer peripheral edge by the claw portions and disposing the medical sheet in a position outside of the lumen of the catheter, causing the medical sheet to remain indwelled in the target site inside the body after the catheter has been extracted from the body.

7. The medical device according to claim 6, wherein the gripping member is inserted into the lumen while being deformed inwardly in a radial direction of the catheter.

8. The medical device according to claim 7, wherein the plurality of support members, when fully protruded from the lumen of the catheter in the protruded state extend in a direction substantially perpendicular to the axis of the lumen.

9. The medical device according to claim 8, wherein the medical sheet is in a folded state while stored in the lumen, and wherein the plurality of support portions surround the medical sheet while the medical sheet is in the folded state.

* * * * *